US00PP13003P2

(12) United States Plant Patent
Cosner et al.

(10) Patent No.: US PP13,003 P2
(45) Date of Patent: Sep. 24, 2002

(54) IMPATIENS PLANTS NAMED 'TILAV'

(76) Inventors: Harlan B. Cosner, 14389 E. Evans Rd., Rogue River, OR (US) 97537; Susan L. Cosner, 14389 E. Evans Rd., Rogue River, OR (US) 97537

( * ) Notice: Subject to any disclaimer, the term of this patent is extended or adjusted under 35 U.S.C. 154(b) by 0 days.

(21) Appl. No.: 09/535,083

(22) Filed: Mar. 23, 2000

(30) Foreign Application Priority Data

Mar. 30, 1999 (CA) ..... 99-1609

(51) Int. Cl.[7] ..... A01H 5/00
(52) U.S. Cl. ..... Plt./317
(58) Field of Search ..... Plt./317

(56) References Cited

U.S. PATENT DOCUMENTS

PP9,615 P * 7/1996 Leue ..... Plt./317

OTHER PUBLICATIONS

UPOV–ROM GTITM computer database, GTI JOUVE retrieval software, citation for 'TiLav' Feb. 2000.*

* cited by examiner

*Primary Examiner*—Bruce R. Campell
*Assistant Examiner*—Anne Marie Grünberg
(74) *Attorney, Agent, or Firm*—Ganz Law, P.C.; Bradley M. Ganz

(57) ABSTRACT

A new and distinct cultivar of 'Impatiens walleriana' plant named 'TiLav', characterized by large lavender fully double flowers, flowers that are positioned above or beyond the foliage, dark green foliage and mounded, freely branching and dense plant habit.

1 Drawing Sheet

BACKGROUND—FIELD OF INVENTION

The present invention relates to a new and distinct cultivar botanically known as 'Impatiens walleriana' and by the cultivar name 'TiLav'.

The cultivar of the photograph was developed and selected in a controlled breeding program in a controlled environment in Coquille, Oreg. by the inventors, Harlan Cosner and Sue Cosner, as described herein.

BACKGROUND—DESCRIPTION OF THE PRIOR ART

The only known cultivar of prior art is named 'Lavender Orchid', subject of U.S. Plant Pat. No. 9,615.

COMPARISON

The impatiens plant of the present invention differs from prior plants, namely 'Lavender Orchid', in at least the following ways:

1. the plant of the present invention has been shown to have a more upright vase shape than 'Lavender Orchid';

2. the stems of the present invention are a much darker color than 'Lavender Orchid';

3. the contrast between the colors of the flowers and foliage is much more pronounced in the present impatiens plants than in 'Lavender Orchid'; and 4. the stems are stronger than those of 'Lavender Orchid'.

These and other characteristics will be apparent to persons skilled in the art.

BACKGROUND—DISCOVERY AND PARENTAGE

The present cultivar was developed by standard cross-pollination. Its seed parent is a semi-double impatiens plant with lavender flowers. This plant was designated 'B-9X-3' (unpatented) under the inventors' controlled breeding program. The pollen parent is a pollen-producing double impatiens plant with lavender flowers. This plant was designated 'B-9X-322' (unpatented) under the inventors' controlled breeding program. The instant plant is both male and female sterile, compared to the male parent, which is only female sterile. The cross was made in the inventors' breeding program, and the first asexual reproduction was made at Coquille, Oreg. Successive asexually reproduced generations have shown the present invention to be stable. Each asexually reproduced generation has been accomplished using cuttings lateral stems with leaves.

The traits of the cultivar of the present invention that have been observed in each successive generation of asexual reproduction and which are unique are the large lavender fully double flowers, flowers that are positioned above or beyond the foliage, dark green foliage and mounded, freely branching and dense plant habit, and both male and female sterility.

Color references are according to The Royal Horticultural Society Colour Chart, except where general terms of ordinary dictionary significance are used.

DETAILED DESCRIPTION

The following observations, measurements and description of the plants and flowers are based on the environmental and cultural practices at Coquille, Oreg. The following measurements, values and comparisons describe plants grown under a double layer of polyethylene film with temperatures typically ranging from about 55° F. to about 85° F. during the daytime. Night heat was provided by bench top set at 62° F. The individual plants were grown in six-inch Azalea containers in a soiless medium. Plants were liquid fed with high nitrate plus trace elements applied at N level 150 PPM of 2 feed, one leach. Plants started in last week of June and finished in late September. Light levels were 4,000 to 6,000 ft. candles.

The plant of the present invention has not been observed in all possible environmental and/or cultural conditions. The phenotype may vary significantly with variations in environment such as temperature, light level, humidity and also with cultural practices such as fertility, soil and water quality.

The accompanying photograph illustrates the overall appearance and the flower color of the cultivar of the present invention described herein. The photograph was taken of a mature plant of 14 weeks of age, during full inflorescence. There may be variations between the colors in the photograph and the colors in the following description due to light reflectance, or the amount of blue or red light captured in the film. If such variations occur, the written description shall control.

Parentage:

The new cultivar was developed by standard cross-pollination. As noted above, its seed parent was a semi-double with lavender flowers; its pollen parent was a pollen-producing double with lavender-colored flowers.

Propagation:

*Type cutting.*—Lateral tips of plants were the cuttings used for asexual reproduction.

*Time to inititate roots.*—Approximately 7 to 14 days at 72° F. soil temperature.

Appearance and form of plant:

*Plant form and habit.*—Upright vase, with a medium vigorous, dense and bushy growing habit.

*Plant size.*—Height is about 26 cm and width is about 30 cm.

*Rooting description.*—The rooting description is characterized by numerous, fibrous and well-branched roots.

*Branching habit.*—Plants are self-branching. Stems are strong and freely produced. The number of stems depends upon cultural practices, age of stems used as cuttings and the number of growth buds present on the cutting when stuck.

*Stems.*—Diameter is about 0.7 cm., and become larger with age. Internode length is about 4.5 cm. Color is close to 147B on more shaded surfaces, with more exposed surfaces marked to heavily marked with, or completely colored 187A.

*Foliage.*—Leaves are simple, generally symmetrical, abundant, alternate and flat. Shape is ovate with attenuate base, acuminate apex, and crenate margin. Texture is smooth and satiny.

*Foliage size.*—Size of the largest leaves is about 6.5 cm in length, and 4.5 cm in width.

*Foliage color.*—Adaxial color is darker than 147A, venation is 147A. Abaxial is 148B with blotches close to 177A, venation is 148A.

*Petioles.*—Petiole shape is half round with a flat upper surface measuring about 3 mm wide, about 2 mm in depth, and about 3 cm in length. Color on the top is streaked with a hard to determine colors that appear close to 146B to 178A, color on the bottom surface is 146B.

*Flower size.*—Diameter of about 4.7 cm, and depth of about 2 cm.

*Flower texture.*—The flower texture is smooth and satiny.

*Flower count.*—Generally 15 or more per stem from visible buds to open flowers at any time during the flowering period.

*Natural flowering season.*—Year around under greenhouse conditions, and the frost-free period from spring until fall outdoors. Flowers are continuously produced throughout the flowering season.

*Duration of flower.*—About four to seven days.

*Time to flower.*—About seven weeks from a rooted cutting.

*Buds.*—Buds are ovate in shape with a length of about 0.8 cm, a width of about 0.6 cm and a depth of about 0.7 cm. Bottom color is 146B on the top and 146D on the bottom.

*Petal size and shape.*—Shape of petals is obovate to exaggerated obovate, entire margin, with obtuse to retuse apex. The largest petals generally consist of 2 petals fused at the base, each is about 2 cm and width is about 2.5 cm.

*Petal color.*—Adaxial surface color of a mature flower is 74D with a dark spot at the base close to 59B. A juvenile flower is close to 74C in color with a dark spot at the base close to 59B. The abaxial surface color is 75A for both mature and juvenile flowers.

*Petal count.*—Numerous, usually 25 or more.

*Spur.*—Shape is acicular tapering, wider at base than apex. Color is 146C at base darkening to a reddish color close to 183B at the apex. Length is about 3 cm and about 2 mm wide at base.

*Calyx.*—The calyx consists of one sepal. The sepal shape is ovate with truncate to cordate base, and acuminate apex, entire margin. Length is about 1 cm and width is about 0.8 cm. Bottom color is close to 145C. Top is 145B to 145C with base spot close to 183C.

*Peduncles.*—Length is about 2 cm and diameter is about 2.5 mm. Color is 148A.

*Pedicels.*—Length is about 2 cm and diameter is about 1.5 mm, generally numbering from 2 to 4 per peduncle with a color of 146B.

*Reproductive organs.*—The plants of the new cultivar are both male and female sterile. No reproductive organs have been found to exist.

*Disease resistance.*—The instant plant has not been tested for disease resistance.

*Rooting ability.*—Easy, no hormones needed.

What is claimed:

1. A new and distinct cultivar of *Impatiens walleriana* as illustrated and as described herein.

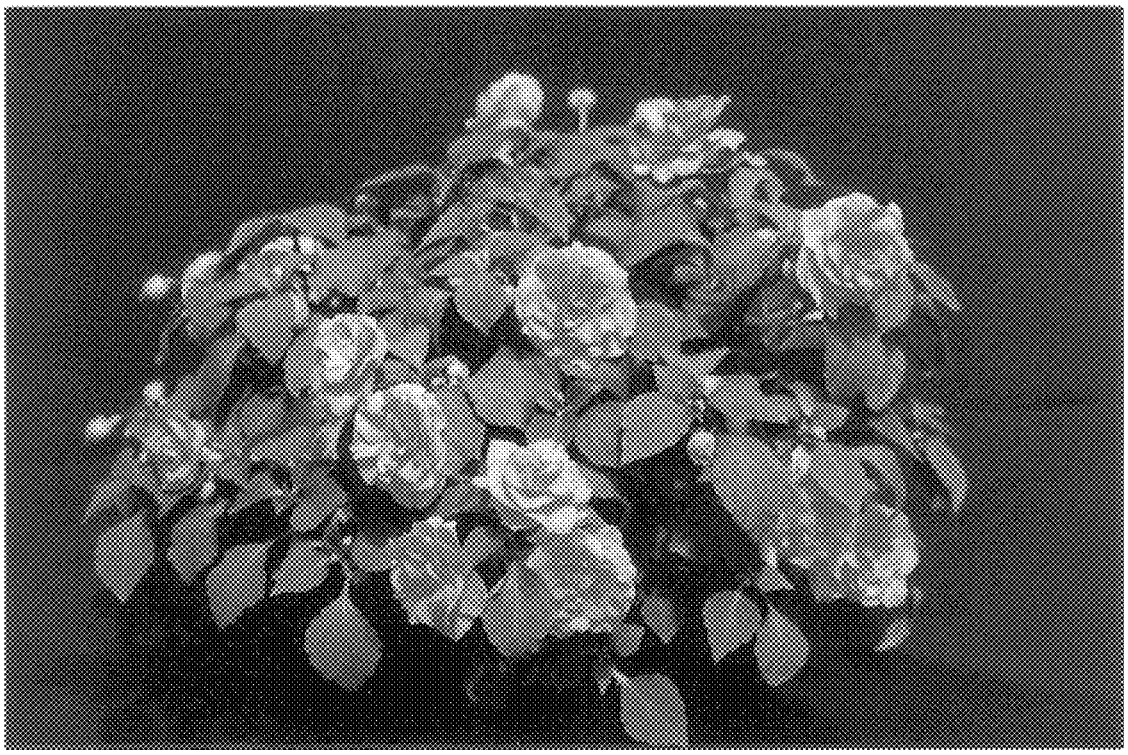

* * * * *